United States Patent [19]

Nadelson

[11] 4,124,714
[45] Nov. 7, 1978

[54] SUBSTITUTED HYDROXY PYRIDONES

[75] Inventor: Jeffrey Nadelson, Denville, N.J.

[73] Assignee: Sandoz, Inc., E. Hanover, N.J.

[21] Appl. No.: 821,989

[22] Filed: Aug. 5, 1977

Related U.S. Application Data

[63] Continuation-in-part of Ser. No. 700,065, Jun. 25, 1976, Pat. No. 4,064,251.

[51] Int. Cl.$^2$ .................... A61K 31/44; C07D 211/30
[52] U.S. Cl. ................................. 424/263; 546/258; 546/257; 546/283; 546/284; 546/115
[58] Field of Search .................. 260/294.8 D, 296 D, 260/296 R, 295 L, 294.8 D, 296 R; 424/263

[56] References Cited

U.S. PATENT DOCUMENTS

| | | | |
|---|---|---|---|
| 3,682,935 | 8/1972 | Law | 260/296 R |
| 3,919,200 | 11/1975 | Berger et al. | 260/296 R |
| 4,024,262 | 5/1977 | Nadelson | 260/297 Z |

Primary Examiner—Henry R. Jiles
Assistant Examiner—Cary Owens
Attorney, Agent, or Firm—Gerald D. Sharkin; Robert S. Honor; Timothy G. Rothwell

[57] ABSTRACT

This disclosure describes novel compounds of the formula:

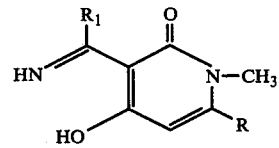

where R is 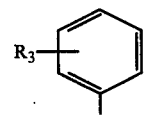 , and $R_1$ is straight chain lower alkyl, or where $R_3$ is hydrogen or halo having an atomic weight of about 19 to 36, which are useful as minor tranquilizers, sleep inducers, muscle relaxants, neuroleptics and anti-ulcer agents.

5 Claims, No Drawings

SUBSTITUTED HYDROXY PYRIDONES

This application is a continuation-in-part of copending application Ser. No. 700,065 filed June 25, 1976, and now U.S. Pat. No. 4,064,251 filed Dec. 20, 1977.

This invention relates to substituted hydroxy pyridones which exhibit minor tranquilizer, sleep inducer, muscle relaxant, neuroleptic and anti-ulcer activity. In particular it relates to 3-substituted-4-hydroxy-6-substituted-1-methyl-2(1H)-pyridones, intermediates thereof and pharmaceutically acceptable salts.

The compounds of this invention may be represented by the following structural formula

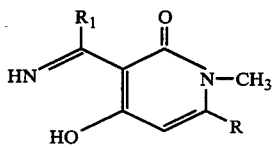  (I)

where R is

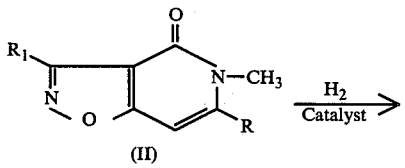, and $R_1$ is straight chain lower alkyl, i.e., straight chain lower alkyl having 1 to 4 carbon atoms, e.g., methyl, ethyl, propyl and the like, or

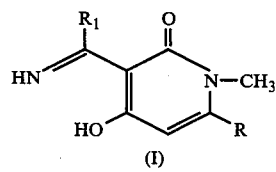

where $R_3$ is hydrogen or halo having an atomic weight of about 19 to 36.

The compounds of formula (I) are prepared according to the following reaction scheme:

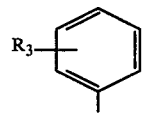

where

R and $R_1$ are as defined above.

The compounds of formula (I) are prepared by reducing a compound of the formula (II) under hydrogen gas in the presence of a catalyst and an inert organic solvent. Although the particular hydrogenation catalyst employed is not critical, the preferred catalysts include palladium on carbon, platinum oxide, Raney nickel, and the like, preferably palladium on carbon. The particular solvent used is not critical, but it is preferred that the reaction be run in the presence of the lower alkanols, e.g., methanol, ethanol, and the like, preferably ethanol.

The temperature of the reaction is not critical, but it is preferred that the reaction be run from about 10° to 50° C., preferably from about 20° to 30° C. The reaction is run from about 1 to 10 hours, preferably from about 2 to 3 hours. The product is recovered using conventional techniques, e.g., filtration.

The compounds of formula (II) are prepared in accordance with the following reaction scheme:

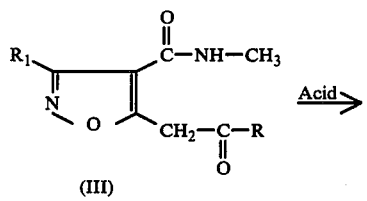

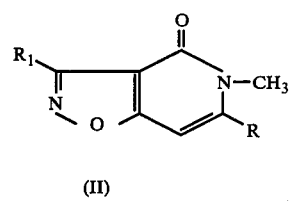

where

R and $R_1$ are as defined above.

The compounds of formula (II) are prepared by treating a compound of the formula (III) with an acid, such as hydrochloric acid, p-toluenesulfonic acid, polyphosphoric acid or sulfuric acid, the latter being especially preferred, in the presence of an inert solvent. Although the particular solvent employed is not critical, the preferred solvents include the aromatic hydrocarbons, such as benzene, toluene and the like, or an excess of the acid utilized above, the latter being especially preferred. The temperature of the reaction is not critical, but it is preferred that the reaction be run from about 80° to 150° C., preferably the reflux temperature of the solvent. The reaction is run from about 12 to 36 hours, preferably from about 20 to 36 hours. The product is recovered using conventional techniques, e.g., column chromatography.

The compounds of formula (III) are prepared according to the following reaction scheme:

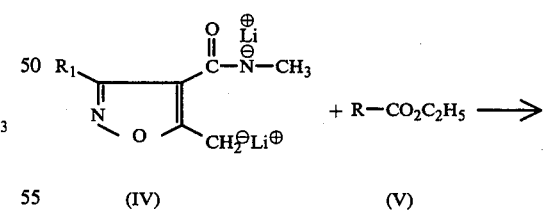

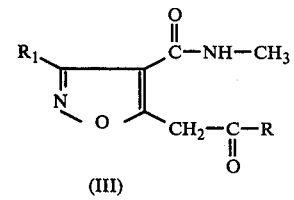

where

R and $R_1$ are as defined above.

The compounds of formula (III) are prepared by treating a compound of the formula (IV) with a compound of the formula (V) in the presence of an inert organic solvent. Although the particular solvent employed is not critical, the preferred solvents include an ether such as diethylether or tetrahydrofuran or an aliphatic hydrocarbon such as pentane, hexane, heptane and the like, preferably tetrahydrofuran. The temperature of the reaction is not critical, but it is preferred that the reaction be run at a temperature of from about $-75°$ to $-55°$ C., preferably from about $-65°$ to $-60°$ C. The reaction is run from about 1 to 5 hours, preferably from about 2.5 to 3.5 hours. The product is recovered using conventional techniques, e.g., trituration followed by filtration.

The compounds of the formula (IV) are prepared in accordance with the following reaction scheme:

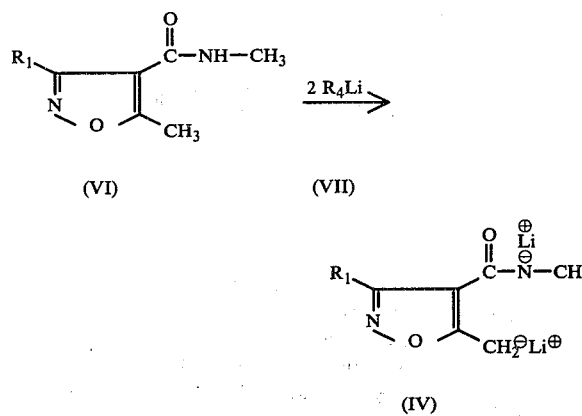

where
$R_4$ is lower alkyl having 1 to 4 carbon atoms, and $R_1$ is as defined above.

The compounds of formula (IV) are prepared by treating a compound of the formula (VI) with a compound of the formula (VII) in the presence of an inert organic solvent. Although the particular solvent employed is not critical, the preferred solvents include an ether such as diethylether or tetrahydrofuran as an aliphatic hydrocarbon such as pentane, hexane, heptane and the like, preferably hexane. The temperature of the reaction is not critical, but it is preferred that the reaction be run at a temperature of from about $-75°$ to $-55°$ C., preferably from about $-65°$ to $-60°$ C. The reaction is run from about 1 to 5 hours, preferably from about 2.5 to 3.5 hours. The compound of formula (IV) is not isolated but employed in situ in the preparation of the compounds of formula (III).

Many of the compounds of formulae (V), (VI) and (VII) are known and may be prepared by methods described in the literature. The compounds of formulae (V), (VI) and (VII) not specifically described may be prepared by analogous methods from known starting materials.

The compounds of formula (I) may also exist in the following tautomeric forms and these tautomeric forms are also considered within the scope of this invention:

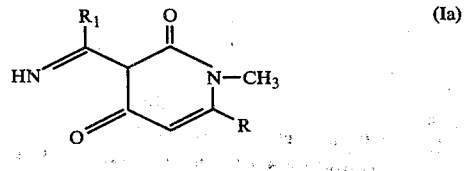

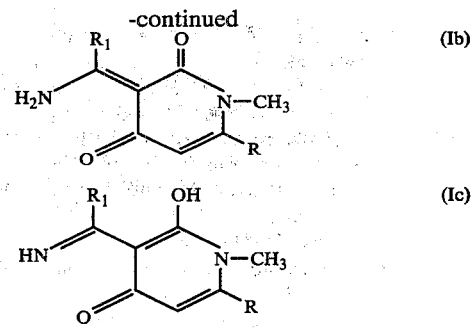

where
R and $R_1$ are as defined above.

Nevertheless, for simplicity, all these tautomeric forms are referred to in the specification and claims as having the formula (I).

The compounds of formula (I) are useful because they possess pharmacological activity in animals as sleep inducers, minor tranquilizers and muscle relaxants as indicated 1) by the hexobarbital reinduction method of Winter, J. Pharmacol. and Exp. Therap., 94, 7-11, 1948, in which the reinduction of anethesia is used to determine sedative-hypnotic acitvity in mice given 70 mg/kg of animal body weight i.p. of hexobarbital followed immediately after the mice regain their righting reflexes by 40.6 to 200 mg/kg of animal body weight i.p. of the test compound; 2) by their ability to produce docility in behavior tests in mice given 50 to 200 mg/kg of animal body weight, i.p. of the test compound according to the 30-word adjective check sheet system basically as described by Irwin S. (Gordon Research Conference, Medicinal Chemistry, 1959) and Chen (Symposium on Sedative and Hypnotic Drugs, Williams and Wilkins, 1954); 3) by their ability to antagonize chlonic convulsions and death in mice given about 50.0 to 250 mg/kg of the test compound followed immediately by 50 mg/kg i.p. of N-sulfamoylazepine; 4) by scoring for loss of righting reflex according to the method of Reed-Muench (American Journal of Hygiene, 27: 493–497, 1938), in which mice are administered 12.5 mg/kg i.p. Thioridazine, immediately after which the test compound is administered at dosages of 38.2 to 100 mg/kg in a volume of 0.1 ml/10 g. body weight. Sixty minutes after dosing, the mice are scored for loss of righting reflex; 5) by the rotarod test as described by Dunham and Miya (J. Am. Pharm. Assoc., 45: 208, 1957); and 6) by the apomorphine gnawing test basically as described by the method of Ernst (Psychopharmacologica, 10: 316 to 323, 1967) in which male wistar rats weighing 90 to 110 g. are given 17.3 mg/kg p.o. of the test compound followed 30 minutes later by 10 mg/kg. i.p. of apomorphine. It is well known that gnawing is induced by apomorphine and the test compound is said to have neuroleptic activity if it reduces the gnawing activity in rats.

The sleep inducing effective dosage of the compounds of formula (I) will vary depending on the particular compound employed. However, in general, satisfactory results are obtained when the compounds are administered orally at a daily dosage of from about 5.0 milligram to about 150 milligrams per kilogram of animal body weight, typically given in a single dose at bedtime. For most large mammals, the total daily dosage is from about 50 to about 1500 milligrams, preferably at bedtime and dosage forms suitable for internal administration comprise from about 12.5 to about 750 milligrams of the compound in admixture with a solid or liquid pharmaceutical carrier or diluent.

For minor tranquilizer use in the treatment of anxiety and tension, the effective dosage will vary depending on the particular compound employed. However, in general, satisfactory results are obtained when the compounds are administered orally at a daily dosage of from aobut 1.0 milligram to about 150 milligrams per kilogram of animal body weight, typically given in divided doses two to four times per day. For most large mammals, the total daily dosage is from about 10 to about 1,500 milligrams, and dosage forms suitable for internal administration comprise from about 2.5 to about 750 milligrams of the compound in admixture with a solid or liquid pharmaceutical carrier or diluent.

For muscle relaxant use in the treatment of muscle spasms, the effective dosage will vary depending on the particular compound employed. However, in general, satisfactory results are obtained when the compounds are administered orally at a daily dosage of from about 5.0 milligram to about 150 milligrams per kilogram of animal body weight, typically given in divided doses two to four times per day. For most large mammals, the total daily dosage is from about 50 to about 1500 milligrams and dosage forms suitable for internal administration comprise from about 12.5 to about 750 milligrams of the compound in admixture with a solid or liquid pharmaceutical carrier or diluent.

For neuroleptic use, the effective dosage will vary depending on the particular compound employed. However, in general, satisfactory results are obtained when the compounds are administered orally at a daily dosage of from about 50.0 milligrams to about 150 milligrams per kilogram of animal body weight, typically given in divided doses two to four times per day. For most large mammals, the total daily dosage is from about 2500 to about 7500 milligrams and dosage forms suitable for internal administration comprise from about 625 to about 3750 milligrams of the compound in admixture with a solid or liquid pharmaceutical carrier or diluent.

For anti-ulcer use, the effective dosage will vary depending on the particular compound employed. However, in general, satisfactory results are obtained when the compounds are administered orally at a daily dosage of from about 10.0 milligrams to about 150 milligrams per kilogram of animal body weight, typically given in divided doses two to four times per day. For most large mammals, the total daily dosage is from about 500 to about 1500 milligrams, and dosage forms suitable for internal administration comprise from about 125 to about 750 milligrams of the compound in admixture with a solid or liquid pharmaceutical carrier or diluent.

For the uses mentioned above, the compounds may be administered orally in such forms as tablets, capsules, elixirs, suspensions and the like or parenterally in the form of an injectable solutions or suspensions. The dosage will vary depending upon the mode of administration utilized and the compound employed.

The compounds of formula (I) may be similarly administered in the form of their non-toxic pharmaceutically acceptable salts. Such salts possess the same order of activity as the nonsalt form and are readily prepared by reacting the molecule with an appropriate acid or an appropriate base by conventional technique and, accordingly, are included within the scope of this invention. Representative of such salts are the mineral acid salts, e.g., hydrochloride, hydrobromide, sulfate and the like, and and the alkali metal salts such as sodium, potassium and the like.

It is to be noted that the compounds of formula (II) in which R represents pyridyl may also exist in salt form. The same salts as described above are applicable to the compounds of formula (II).

Tablets and capsules containing the ingredients indicated below may be prepared by conventional techniques and are useful as sleep inducers at a dose of one or two tablets just before bedtime. Tablets and capsules containing the ingredients indicated below may also be useful as minor tranquilizers, muscle relaxants, neuroleptic and anti-ulcer agents in divided doses two to four times per day.

| Ingredients | Weight (mg.) tablet | capsule |
|---|---|---|
| 3-(α-iminobenzyl)-4-hydroxy-6-(2-pyridyl)-1-methyl-2(1H)-pyridone | 200 | 200 |
| tragacanth | 10 | — |
| lactose | 247.5 | 300 |
| corn starch | 25 | — |
| talcum | 15 | — |
| magnesium stearate | 2.5 | — |
| TOTAL | 500 mg. | 500 mg. |

EXAMPLE 1.

3-Phenyl-5-(2-pyridylcarbonylmethyl)-N-methyl-isoxazole-4-carboxamide.

A suspension of 28 g. (0.13 mole) of 3-phenyl-N,5-dimethyl-isoxazole-4-carboxamide and 330 milliliters of tetrahydrofuran is cooled to −65° C. and 180 milliliters of 1.6M n-butyllithium in hexane (0.288 mole) is added dropwise, maintaining the temperature between −60° and −70° C. After the addition is complete, the organic suspension is stirred for 1½ hours at −60° to −70° C., and then 19.6 g. (0.13 mole) of ethyl picolinate in 196 ml. tetrahydrofuran is added dropwise maintaining the temperature between −60° and −70° C. After addition is complete, the mixture is stirred 1½ hours at −60° to −70° C. and then warmed to −30° C. and quenched by the addition of saturated ammonium chloride solution. The mixture is further diluted with tetrahydrofuran and the layers are separated. The tetrahydrofuran layer is washed twice with 50% brine, and once with brine, dried over anhydrous magnesium sulfate, filtered and evaporated in vacuo. The solid residue is triturated with ether and filtered to give 3-phenyl-5-(2-pyridylcarbonylmethyl)-N-methyl-isoxazole-4-carboxamide; m.p. 146° to 149° C.

Following the above procedure and using in place of 3-phenyl-5,N-dimethyl-isoxazole-4-carboxamide, an equivalent amount of
 (a) 3-(p-chlorophenyl)-5,N-dimethyl-isoxazole-4-carboxamide,
 (b) 3-(p-fluorophenyl)-5,N-dimethyl-isoxazole-4-carboxamide,
 (c) 3-ethyl-5,N-dimethyl-isoxazole-4-carboxamide,
there is obtained
 (a) 3-(p-chlorophenyl)-5-(2-pyridylcarbonylmethyl)-N-methyl-isoxazole-4-carboxamide,
 (b) 3-(p-fluorophenyl)-5-(2-pyridylcarbonylmethyl)-N-methyl-isoxazole-4-carboxamide, or (c) 3-ethyl-5-(2-pyridylcarbonylmethyl)-N-methyl-N-methyl-isoxazole-4-carboxamide, respectively.

Again following the same procedure and using in place of ethyl picolinate an equivalent amount of
- (d) nicotinate ethyl ester,
- (e) isonicotinate ethyl ester,
- (f) 2-thiophene carboxylic acid ethyl ester, or
- (g) 2-furane carboxylic acid ethyl ester there is obtained
- (d) 3-phenyl-5-(4-pyridylcarbonylmethyl)-N-methyl-isoxazole-4-carboxamide,
- (e) 3-phenyl-5-(3-pyridylcarbonylmethyl)-N-methyl-isoxazole-4-carboxamide,
- (f) 3-phenyl-5-(2-thienylcarbonylmethyl)-N-methyl-isoxazole-4-carboxamide, or
- (g) 3-phenyl-5-(2-furylcarbonylmethyl)-N-methyl-isoxazole-4-carboxamide, respectively.

Furthermore, following the same procedure as outlined above and using in place of 3-phenyl-5,N-dimethyl-isoxazole-4-carboxamide an equivalent amount of 3-ethyl-5,N-dimethyl-isoxazole-4-carboxamide, and in place of ethyl picolinate an equivalent amount of
- (d) nicotinate ethyl ester,
- (e) isonicotinate ethyl ester,
- (f) 2-thiophene carboxylic acid ethyl ester, or
- (g) 2-furane carboxylic acid ethyl ester there is obtained
- (h) 3-ethyl-5-(4-pyridylcarbonylmethyl)-N-methyl-isoxazole-4-carboxamide,
- (i) 3-ethyl-5-(3-pyridylcarbonylmethyl)-N-methyl-isoxazole-4-carboxamide,
- (j) 3-ethyl-5-(2-thienylcarbonylmethyl)-N-methyl-isoxazole-4-carboxamide, or
- (k) 3-ethyl-5-(2-furylcarbonylmethyl)-N-methyl-isoxazole-4-carboxamide, respectively.

EXAMPLE 2.

5-Methyl-3-phenyl-6-(2-pyridyl)-isoxazolo[4,5-c]pyridin-4(5H)-one.

A mixture of 20.1 g. (0.0627 mole) of 3-phenyl-5-(2-pyridylcarbonylmethyl)-N-methyl-isoxazole-4-carboxamide and 200 ml. of 2M sulfuric acid is refluxed for 24 hours. The mixture is cooled and made basic with 2N sodium hydroxide and then extracted with methylene chloride. The methylene chloride layer is washed with water, dried over anhydrous magnesium sulfate, filtered and evaporated in vacuo. The resulting solid is purified by column chromatography to give 5-methyl-3-phenyl-6-(2-pyridyl)-isoxazolo[4,5-c]pyridin-4-(5H)-one; m.p. 160° to 162° C.

Following the above procedure and using in place of 3-phenyl-5-(2-pyridylcarbonylmethyl)-N-methyl-isoxazole-4-carboxamide, an equivalent amount of
- (a) 3-(p-chlorophenyl)-5-(2-pyridylcarbonylmethyl)-N-methyl-isoxazole-4-carboxamide,
- (b) 3-(p-fluorophenyl)-5-(2-pyridylcarbonylmethyl)-N-methyl-isoxazole-4-carboxamide,
- (c) 3-ethyl-5-(2-pyridylcarbonylmethyl)-N-methyl-isoxazole-4-carboxamide,
- (d) 3-phenyl-5-(4-pyridylcarbonylmethyl)-N-methyl-isoxazole-4-carboxamide,
- (e) 3-phenyl-5-(3-pyridylcarbonylmethyl)-N-methyl-isoxazole-4-carboxamide,
- (f) 3-phenyl-5-(2-thienylcarbonylmethyl)-N-methyl-isoxazole-4-carboxamide,
- (g) 3-phenyl-5-(2-furylcarbonylmethyl)-N-methyl-isoxazole-4-carboxamide,
- (h) 3-ethyl-5-(4-pyridylcarbonylmethyl)-N-methyl-isoxazole-4-carboxamide,
- (i) 3-ethyl-5-(3-pyridylcarbonylmethyl)-N-methyl-isoxazole-4-carboxamide,
- (j) 3-ethyl-5-(2-thienylcarbonylmethyl)-N-methyl-isoxazole-4-carboxamide, or
- (k) 3-ethyl-5-(2-furylcarbonylmethyl)-N-methyl-isoxazole-4-carboxamide, there is obtained
- (a) 5-methyl-3-(p-chlorophenyl)-6-(2-pyridyl)-isoxazolo[4,5-c]pyridin-4(5H)-one,
- (b) 5-methyl-3-(p-fluorophenyl)-6-(2-pyridyl)-isoxazolo[4,5-c]pyridin-4(5H)-one,
- (c) 5-methyl-3-ethyl-6-(2-pyridyl)-isoxazolo[4,5-c]pyridin-4(5H)-one,
- (d) 5-methyl-3-phenyl-6-(4-pyridyl)-isoxazolo[4,5-c]pyridin-4(5H)-one,
- (e) 5-methyl-3-phenyl-6-(3-pyridyl)-isoxazolo[4,5-c]pyridin-4(5H)-one,
- (f) 5-methyl-3-phenyl-6-(2-thienyl)-isoxazolo[4,5-c]pyridin-4(5H)-one,
- (g) 5-methyl-3-phenyl-6-(2-furyl)-isoxazolo[4,5-c]pyridin-4(5H)-one,
- (h) 5-methyl-3-ethyl-6-(4-pyridyl)-isoxazolo[4,5-c]pyridin-4(5H)-one,
- (i) 5-methyl-3-ethyl-6-(3-pyridyl)-isoxazolo[4,5-c]pyridin-4(5H)-one,
- (j) 5-methyl-3-ethyl-6-(2-thienyl)-isoxazolo[4,5-c]pyridin-4(5H)-one, or
- (k) 5-methyl-3-ethyl-6-(2-furyl)-isoxazolo[4,5-c]pyridin-4(5H)-one, respectively.

EXAMPLE 3.

3-(α-iminobenzyl)-4-hydroxy-6-(2-pyridyl)-1-methyl-2(1H)-pyridone.

A mixture of 16.5 g. (0.0545 mole) of 5-methyl-3-phenyl-6-(2-pyridyl)-isoxazolo[4,5-c]pyridin-4(5H)-one, 330 ml. ethanol and 1.65 g. 10% palladium on carbon is hydrogenated at 50 psi and room temperature. The hydrogenation is ceased after one equivalent of hydrogen is absorbed (ca. 2.5 hours). The mixture is treated with methylene chloride and the catalyst is removed by filtration. The solvents are removed in vacuo to a volume of ca. 50 ml. and then ether is added, to precipitate solids which are removed by filtration to give 3-(α-iminobenzyl)-4-hydroxy-6-(2-pyridyl)-1-methyl-2(1H)-pyridone; m.p. 242° to 245° C. In order to obtain the sodium salt of the aforementioned compound, for example, the compound is dissolved in methanol and treated with sodium hydroxide solution to yield after evaporation the sodium salt.

Following the above procedure and using in place of 5-methyl-3-pyridyl-6-(2-pyridyl)-isoxazolo[4,5-c]pyridin-4(5H)-one an equivalent amount of
- (a) 5-methyl-3-(p-chlorophenyl)-6-(2-pyridyl)-isoxazolo[4,5-c]pyridin-4(5H)-one,
- (b) 5-methyl-3-(p-fluorophenyl)-6-(2-pyridyl)-isoxazolo[4,5-c]pyridin-4(5H)-one,
- (c) 5-methyl-3-ethyl-6-(2-pyridyl)-isoxazolo[4,5-c]pyridin-4(5H)-one,
- (d) 5-methyl-3-phenyl-6-(4-pyridyl)-isoxazolo[4,5-c]pyridin-4(5H)-one,
- (e) 5-methyl-3-phenyl-6-(3-pyridyl)-isoxazolo[4,5-c]pyridin-4(5H)-one,
- (f) 5-methyl-3-phenyl-6-(2-thienyl)-isoxazolo[4,5-c]pyridin-4(5H)-one, (g) 5-methyl-3-phenyl-6-(2-furyl)-isoxazolo[4,5-c]pyridin-4(5H)-one,
(h) 5-methyl-3-ethyl-6-(4-pyridyl)-isoxazolo[4,5-c]pyridin-4(5H)-one,
(i) 5-methyl-3-ethyl-6-(3-pyridyl)-isoxazolo[4,5-c]pyridin-4(5H)-one,
(j) 5-methyl-3-ethyl-6-(2-thienyl)-isoxazolo[4,5-c]pyridin-4(5H)-one, or
(k) 5-methyl-3-ethyl-6-(2-furyl)-isoxazolo[4,5-c]pyridin-4-(5H)-one there is obtained (a) 3-(α-imino-p-chlorobenzyl)-4-hydroxy-6-(2-pyridyl)-1-methyl-2(1H)-pyridone,
(b) 3-(α-imino-p-fluorobenzyl)-4-hydroxy-6-(2-pyridyl)-1-methyl-2(1H)-pyridone,
(c) 3-(1-iminopropyl)-4-hydroxy-6-(2-pyridyl)-1-methyl-2(1H)-pyridone,
(d) 3-(α-iminobenzyl)-4-hydroxy-6-(4-pyridyl)-1-methyl-2(1H)-pyridone,
(e) 3-(α-iminobenzyl)-4-hydroxy-6-(3-pyridyl)-1-methyl-2(1H)-pyridone,
(f) 3-(α-iminobenzyl)-4-hydroxy-6-(2-thienyl)-1-methyl-2(1H)-pyridone,
(g) 3-(α-iminobenzyl)-4-hydroxy-6-(2-furyl)-1-methyl-2(1H)-pyridone,
(h) 3-(1-iminopropyl)-4-hydroxy-6-(4-pyridyl)-1-methyl-2(1H)-pyridone,
(i) 3-(1-iminopropyl)-4-hydroxy-6-(3-pyridyl)-1-methyl-2(1H)-pyridone,
(j) 3-(1-iminopropyl)-4-hydroxy-6-(2-thienyl)-1-methyl-2(1H)-pyridone, or
(h) 3-(1-iminopropyl)-4-hydroxy-6-(2-furyl)-1-methyl-2(1H)-pyridone, respectively.

The 3-(α-iminobenzyl)-4-hydroxy-6-(2-pyridyl)-1-methyl-2(1H)-pyridone of this example is an effective muscle relaxant and minor tranquilizer when orally administered to an animal in need of said treatment at a dosage of 100 mg. two to four times per day. The compound of this example is also effective as a sleep inducer when orally administered to an animal in need of said treatment at a dosage of 200 mg. just before bedtime.

What is claimed is:

1. A compound of the formula

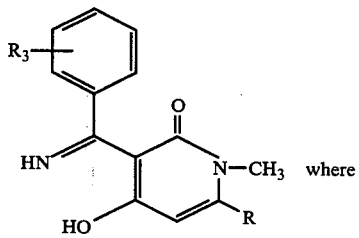

where R is

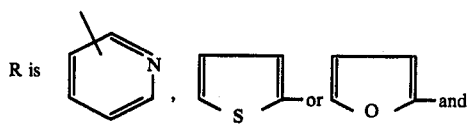

where R is

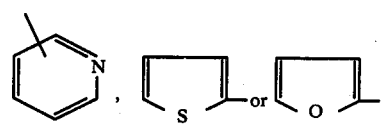

and R$_3$ is hydrogen or halo having an atomic weight of about 19 to 36, or a pharmaceutically acceptable salt thereof.

2. A compound of the formula

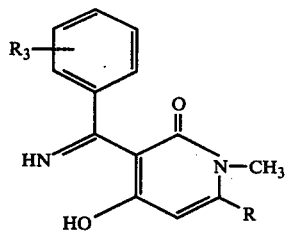

where R is

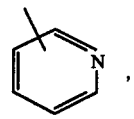

and R$_3$ is as defined in claim 1, or a pharmaceutically acceptable salt thereof.

3. The compound of claim 1 which is 3-(α-iminobenzyl)-4-hydroxy-6-(2-pyridyl)-1-methyl-2(1H)-pyridone.

4. A method of treating muscle spasms which comprises administering to a mammal in need of said treatment a muscle-relaxant effective amount of a compound according to claim 1.

5. A pharmaceutical composition for use in treating muscle spasms comprising an effective amount of a compound of claim 1 and a pharmaceutically acceptable carrier therefor.

* * * * *